(12) United States Patent
Loria et al.

(10) Patent No.: US 7,048,928 B2
(45) Date of Patent: May 23, 2006

(54) ANTI-ALLERGIC PHARMACEUTICAL COMPOSITION CONTAINING AT LEAST ONE ALLERGEN AND AT LEAST ONE ANTIHISTAMINE COMPOUND

(75) Inventors: Emile Loria, Toulouse (FR); Gaetan Terrasse, Saint-Valier (FR); Yves Trehin, Toulouse (FR)

(73) Assignee: Antialis, St. Vallier (FR)

( * ) Notice: Subject to any disclaimer, the term of this patent is extended or adjusted under 35 U.S.C. 154(b) by 96 days.

(21) Appl. No.: 09/867,159

(22) Filed: May 29, 2001

(65) Prior Publication Data

US 2003/0104013 A1      Jun. 5, 2003

(30) Foreign Application Priority Data

Mar. 30, 2001  (FR)  .................... 01 04370
May 3, 2001   (FR)  .................... 01 05929

(51) Int. Cl.
*A61K 39/02*   (2006.01)
*A61K 39/35*   (2006.01)
*A61K 38/08*   (2006.01)

(52) U.S. Cl. .................. 424/185.1; 424/275.1; 530/328

(58) Field of Classification Search ............. 424/185.1, 424/275.1; 536/23.5; 435/320.1
See application file for complete search history.

(56) References Cited

U.S. PATENT DOCUMENTS

| | | | |
|---|---|---|---|
| 4,302,458 A | * | 11/1981 | Chazerain et al. |
| 5,256,680 A | * | 10/1993 | Connor et al. .............. 514/364 |
| 5,433,948 A | * | 7/1995 | Thomas et al. .......... 424/185.1 |
| 5,814,345 A | * | 9/1998 | Beck et al. |
| 5,820,862 A | * | 10/1998 | Garman et al. .......... 424/184.1 |
| 5,827,852 A | * | 10/1998 | Russell et al. |
| 6,258,816 B1 | * | 7/2001 | Singh et al. |
| 6,319,513 B1 | * | 11/2001 | Dobrozsi et al. |
| 6,455,686 B1 | * | 9/2002 | McCall et al. |

OTHER PUBLICATIONS

Stryer et al, in Biochemistry, Third edition, W H Freeman Company, New York, pp. 31-33, 1998.*
Ngo et al, 1994, The Protein Folding Problem and Tertiary Structure Prediction, pp. 492-495.*
Fasler et al, J Allergy Clin Immunology 101(4): 521-530, Apr. 1998.*
Webster's II New Riverside University Dictionary, p. 933, 1984.*
Hoyne et al, Immunology and Cell Biology 74: 180-186, 1996.*
Ginkel et al, J Immunol 159(2): 685-93, Jul. 1997.*
Hsu et al, Int Immunol 8(9): 1405-11, Sep. 1996.*
Attwood et al, The Babel of Bioinformatics, 2000, Science vol. 290 No. 5491: 471-473.*
Whisstock et al, Quarterly Reviews of Biophysics 36(3): 307-340, 2003.*
Verma et al, Nature 389: 239-242, Sep. 1997.*

* cited by examiner

*Primary Examiner*—Christina Chan
*Assistant Examiner*—Phuong Huynh
(74) *Attorney, Agent, or Firm*—Mandel & Adriano

(57) ABSTRACT

The present invention relates to an anti-allergic pharmaceutical composition containing at least two active agents chosen from among: (i) one allergen, (ii) one antihistamine compound, and (iii) one inhibitor of histamine synthesis. The active agents are associated in the composition with a pharmaceutically acceptable vehicle.

10 Claims, No Drawings

ANTI-ALLERGIC PHARMACEUTICAL COMPOSITION CONTAINING AT LEAST ONE ALLERGEN AND AT LEAST ONE ANTIHISTAMINE COMPOUND

BACKGROUND OF THE INVENTION (1) Field of the Invention

The present invention relates to new pharmaceutical compositions for the prevention and treatment of allergies. Allergies are a scourge which affects 25% of the world's population. This number is on the increase in connection with growing environmental toxicity (dust, food, motor vehicles). In addition, a person's risk of suffering from allergy is increased if there is a previous family history of allergy.

(2) Prior Art

The biological mechanism of allergies may be described as an abnormally amplified reaction to the entry of an allergen into the body. The following events account for the reaction:

identification of the allergen by the body, secretion of cytokines in response to allergen penetration, conversion of Th1 cells into Th2 cells, with the production of clones specific to the antigen, the Th2 cells synthesize interleukins 4 and 13, responsible for aggravation of the allergic symptoms through an upsurge in IgE synthesis the terminal phase of the reaction is the release of histamine and serotonin having a recruiting effect on the Th2 clones.

toxic and inflammatory self-maintaining reaction, even without any antigen stimulation.

The antigen-presenting cells (APCs: macrophages, dendritic cells, B-lymphocytes) take part in the reaction of hypersensitivity through basic cell cooperation carrying the immune reaction further. Allergies belong to the nonself class of defense mechanisms. The main allergens are acarids (dust mites) (80%) and pollens (20%).

The self-stimulating reactions of specific APC clones have an effect on the general rate of release of histamine and serotonin leading to an aggravation of the general clinical symptomatology.

The recruitment level of new Ige-secreting cells is thereby increased, facilitating the explosion of clinical signs when a new allergen penetrates inside the body. This can be seen in atopic persons in whom allergic reactions are severe owing to the high level of Th2 clones promoting the synthesis of IgE.

The general reaction observed subsequent to the penetration of the new allergen is not due to its toxicity but simply to the fact that the triggering level of allergic phenomena is very low, helped by other sensitizations.

An allergy is a reaction due to hypersynthesis of IgE immunoglobulins. The inflammatory reaction chiefly affects the respiratory and ENT spheres, with pathological focalization at the nose, lungs and skin. Pathologies associated with the allergy are invalidating and suffer from the lack of efficacy of conventional treatment. There is no preventive strategy and curative means are insufficient or ill used.

The usual treatment of allergic disease consists, during a first phase, of identifying the allergen responsible such as dust mites, pollen, mold, or food. The second phase comprises removal measures. The third phase or treatment phase focuses on the target organ which appears to be symptomatic e.g., ENT treatment for rhinitis, anti-asthmatic treatment if the affected sphere is respiratory, dermatological treatment if the affected areas are skin areas.

In the event of failure of the preceding measures, individual or complementary treatment may be offered through the choice of a specific immunotherapy, i.e. specific pollen, specific acarid, specific mold. The complexity of the treatment instituted makes it difficult to follow. A succession of treatments is a patent factor of failure.

SUMMARY OF THE INVENTION

The purpose of the present invention is precisely to offer new means of treating allergies that are both preventive and curative.

This purpose is achieved by treating the two main sides of the immune reaction: firstly, the upstream part of the immune response which, after presenting the antigen to the APCs, leads to increased synthesis of the IgEs responsible for the self-recruiting of the immunity cells, and secondly, the downstream side of the immune response which leads to release of the preformed mediators, essentially histamine, responsible for the final clinical outcome.

The optional combined use of an inhibitor of histamine synthesis makes it possible to reduce the concentration of the latter and therefore to improve the therapeutic efficacy of the pharmaceutical composition according to the invention.

The present invention concerns an anti-allergic pharmaceutical composition containing at least two active agents chosen from among: (i) one allergen, (ii) one antihistamine compound, and (iii) one inhibitor of histamine synthesis, with said active agents being associated in said composition with a pharmaceutically acceptable vehicle.

DETAILED DESCRIPTION OF THE PREFERRED EMBODIMENT(S)

The subject of the invention is more particularly an anti-allergic pharmaceutical composition containing (i) at least one allergen and (ii) at least one antihistamine compound, and optionally (iii) at least one inhibitor of histamine synthesis, in a pharmaceutically acceptable vehicle.

A first preferred form of an anti-allergic pharmaceutical composition according to the invention contains (i) at least one allergen and (ii) at least one antihistamine compound, in a pharmaceutically acceptable vehicle, enabling release of peptides and other chemical substances in an independent manner at galenic level.

Advantageously, the allergen is chosen from among the major antigens or a mixture of major antigens of acarids able to induce an immune reaction. The research conducted within the scope of the invention consisted of using ubiquitous antigens of acarids. These antigens are present in substantial quantity in the environment and are the cause of the development of allergic reactions in the world. Two acarids, *D. Pteronyssinus* (DP) and *D. Farinae* (DF) are the most represented in the world environment.

The present invention most particularly gives consideration to a cystine protease as an allergen, the carrier of antigenicity which is 90% identical for these two acarids. The epigenic and amino acid sequences of the cystine protease of *D. Pteronyssinus* (DP) are shown in the list of appended sequences given respectively under numbers SEQ ID NO: 1 and SEQ ID NO: 2.

The allergens used in the compositions of the invention may either be extracts obtained from crude biological material, or wholly or partly purified proteins optionally produced by genetic engineering or by peptide synthesis.

Therefore the invention further concerns, as an allergen, the peptide epitopes of cystine protease. Three epitopic parts have been identified which form triggering agents for the immune response. These are the three peptides with the following sequences:

| | |
|---|---|
| RMQGGCGSCN | (SEQ ID NO:3) |
| QPNYHAVNIV | (SEQ ID NO:4) |
| WTVRNSWDT | (SEQ ID NO:5) | and their possible analogues.

The sequences of the protein epitopes cited above may contain primers and supplementary amino acid sequences or substitutions facilitating their adhesion to the Major Histocompatibility Complex (MHC).

The invention gives special consideration to pharmaceutical compositions containing at least one of these peptides as an allergen.

These peptide epitopes are strictly identical in DF and DP, and in other acarids, since they are carriers of the enzyme function of cystine protease. Their lipophilia, and the fact that they tolerate the enzyme function, account for the fact that these epitope parts are constant from one species of acarid to another and that they are the site of a general immune response.

The use of these parts, either in the form of cycled proteins, or in epigenic form, or even in their RNA form, induce tolerance to the natural antigen and reduce the general level of the immune response upstream.

Cyclizing the epitopes and/or inclusion of the epigenic patterns in a longer sequence makes it possible to improve the presentation of the antigens to the T-lymphocytes. This improved presentation will allow presentation of the antigens and epitopes to the MHC and thereby trigger the immune tolerance response. The antigens must previously be rearranged by the APCs. The simple epitopic form does not allow rearrangement by the APCs since, as a general rule, only a protein longer than 10 amino acids may be cut and presented by the APCs to the T-lymphocytes.

These peptides may be associated with any pharmaceutically acceptable vector, for example, of phospholipid type.

If epigens are involved, the latter may be primed by the following nucleotide sequence: 5'GCGGCGGCG 3' (SEQ ID NO: 6).

The controlled reaction of the TH2/TH1 switch induced by this protein, or its epigen, may also be achieved using other methods, in particular with the nucleotide primers according to the following sequence 5'TGAGCGGCGGCG 3' (SEQ ID NO: 7), and using any other method allowing upstream control of the TH2/TH1 switch.

It is therefore possible to integrate the epigens corresponding to the epitopes of DP/DF with a nucleotide primer sequence of sequence (SEQ ID NO: 7) by alternating said sequence (SEQ ID NO: 7) and an epitope so as to integrate the three major epitopes of DP/DF, either together or separately.

The integration of the epitopes together leads to obtaining a group made up of a first nucleotide primer sequence (SEQ ID NO: 7), a first major epitope, a second nucleotide primer sequence (SEQ ID NO: 7), a second major epitope, a third nucleotide primer sequence (SEQ ID NO: 7), and a third major epitope.

The integration of epitopes separately leads to mixing three groups each made up of a nucleotide primer sequence (SEQ ID NO: 7) and a major epitope. This integration of the epitopes with a nucleotide primer sequence according to the following sequence (SEQ ID NO: 7) improves the efficacy with which the DP/DF epigens are presented to the T-lymphocytes. With this improved presentation, the DP/DF epigens will stimulate the TH1 switch and, therefore, reduce the level of the allergic response.

The use of these epitopes, or of a solution enabling the TH1/TH2 switch, such as the nucleotide primers of sequence (SEQ ID NO: 7), and their association with an antihistamine compound, and optionally with an inhibitor of histamine synthesis, provide an efficient, innovative solution for the prevention and treatment of allergies.

Consequently, the compositions of the present invention comprise an efficient quantity of at least one allergen, such as defined above, without predicting the role of this allergen in the patient's symptomatology.

With this approach, it is possible to have global access to the allergic illness without giving consideration to the specificity of the allergen. Indeed, with the composition of the invention, it is possible to treat a level of immune reactivity and not to propose a specific immunotherapy.

The use of the allergen, under the different forms described above, in the compositions of the present invention means that it is possible to induce tolerance to the natural antigen and to reduce the general level of immune response upstream. However, as mentioned previously, the allergen cannot alone cure the allergy since the toxic, inflammatory terminal reaction subsists, which is self-maintaining without antigen stimulation. This reaction must also be treated by blocking the terminal phase of the allergy. Blocking the histamine receptors is the main effector mechanism. This blocking must be made over a time interval that is sufficiently long for there to be a negative feedback on the synthesis of these receptors. Antihistamines are anti-receptor molecules of choice to block this terminal reaction. Therefore, the compositions of the invention, in addition to the allergen, contain an antihistamine compound, and, optionally, an inhibitor of histamine synthesis.

Suitable antihistamine compounds may be made of: brompheniramine, cetirizine, fexofenadine, cyproheptadine, dexchlorpheniramine, hydroxizine, ketotifene, loratidine, mequitazine, oxotomide, mizolastine, ebastine, astemizole, carbinoxamide, alimemazine, buclizine, cyclizine hydrochlorate, and/or doxylamine.

As indicated above, the allergy is also accompanied by increased synthesis of histamine, which also causes self-maintaining of the terminal inflammatory reaction. This histamine synthesis may possibly be controlled, in order to improve the efficacy of the previously proposed pharmaceutical composition. This control has recourse to the inhibition of histamine synthesis. Consequently, the compositions of the invention contain an efficient quantity of an antihistamine compound which may optionally be associated with an inhibitor of histamine synthesis. Therefore, blocking of the terminal histamine effector mechanisms will provide efficient control over the final cascade of the allergic reaction. The terminal route for the synthesis and stimulation of histamine receptors must therefore be blocked in global manner for the composition to have improved efficacy.

A particular form of implementation of the invention consists in an anti-allergic pharmaceutical composition containing at least one antihistamine compound and at least one inhibitor of histamine synthesis, with said compounds being associated in said composition with a pharmaceutically acceptable vehicle.

As inhibitors of histamine synthesis, mention may be made of an inhibitor of histidine decarboxylase such as tritoqualine.

By preventing histamine synthesis, the inhibitor of histidine decarboxylase increases the efficiency of the composition in its action on the downstream side of the allergies' biological mechanism by complementing the antihistamine compound.

The compositions of the invention provide a new allergen approach providing preventive vaccination against the development of allergic illnesses. The object is to restore a silent defense homeostasis to the body in relation to its environment.

The compositions of the present invention contain a quantity of allergens on the order of 1 to 1500 μg and, advantageously, from 10 to 150 μg. Concerning the peptides, each one is advantageously present in proportions in the range of 1 to 1500 μg so as to slow down the immunological response leading to increased IgE synthesis.

The antihistamine compound is present in the compositions of the invention in a proportion on the order of 1 to 2000 mg.

In the case of a composition according to the invention containing an antihistamine compound and an inhibitor of histamine synthesis, these compounds are present in a proportion on the order of: 5 to 200 mg of antihistamine compound, and 10 to 300 mg of an inhibitor of histidine decarboxylase such as tritoqualine.

The compositions of the present invention may be presented in either a form for transdermal application, such as an ointment for children, a form for oral administration, such as a slow release product, or in gastro-resistant tablet form or gum form. They may also be in spray or eye lotion form, or galenic forms with programmed mucosal and secondarily per os disintegration.

The different compositions of the invention can be administered by several routes chosen in accordance with the patient's pathological profile and age. For children, they can be administered in patch form, syrup form or tablets to be dissolved in the mouth. Other forms, such as eye lotion or injection may also be used. In adults, all galenic forms can be contemplated.

The advantages of a coupled form include simplicity of treatment, patient compliance with the simplified treatment, and a more successful outcome.

This solution also makes it possible to prevent the allergic illness and not only patent pathological conditions. Children of allergic parents could be the major target of this preventive treatment. The result would be shorter hospital stays, fewer antibiotic treatments, and improved quality of life. Indeed the TH2/TH1 switch must occur as early as possible in order to be effective, since in infants it is the TH2 route which predominates, and is responsible for hyper-response to the environment. The TH2/TH1 switch must occur early for its duration to be as long as possible, since antigenic stimulation by the antigens of the environment (e.g. dust mites and bacteria) are stimulators of the TH2 route.

The pharmaceutical composition of the present invention is particularly useful for the preparation of a medicinal product intended to treat allergic hypersensitive reactions.

Advantageously, the pharmaceutical composition of the present invention is in a galenic form with programmed mucosal or sublingual and secondarily per os disintegration.

The pharmaceutical composition of the present invention is also useful for the preparation of a medicinal product intended to treat or prevent allergic hypersensitivity reactions, and to treat or prevent allergic asthma, allergic rhinitis and atopic and allergic eczema.

Finally, the pharmaceutical composition of the present invention is particularly useful for the preparation of a medicinal product intended to treat or prevent allergic symptoms in children, infants, and adults.

Other advantages and characteristics of the invention will become apparent on reading the clinical observations made in the treatment of allergic patients as recorded in the table given below.

These observations were made on approximately one hundred patients who were given a composition of the invention associating at least one allergen and an antihistamine compound.

Patient age ranged from 7 to 60 years. They all were presented with at least one positive dust mite or pollen prick test, and symptomatology of rhinitis or asthma of at least one year's onset.

The pathological profile of the patients was classified according to the following typology comprising three descriptive categories: inflammation, secretion and the figured element.

Only clinical examination was used to classify inflammation. It was considered that there was inflammation if examination of the mucosa or target organs showed redness confirming an inflammatory phenomenon, Secretion concerned the observation of an exudate whether purulent or non-purulent affecting a target organ (e.g. mucosa, skin, etc . . . ).

The figured element concerned a change in the structure of the organ under consideration, which may occur in several pathological forms. Consideration was only given to the existence of a change without going into the detail of this change.

The grading of pathological severity used a scale of 1 to 4 measuring intensity as a fraction e.g. ¼ or ½, or a whole number.

According to this grading, an assessment of ¼ denotes target organ impairment of between 0 and less than ¼. An assessment of ½ denotes target organ impairment of between ¼ and one half; an assessment of ¾ denotes target organ impairment of more than one half and less than ¾; an assessment of 1 denotes impairment of more than ¾.

A first category of target organs was graded according to this typology. It comprises the eyes, nose, pharynx, larynx and the skin.

In respect of the lungs, the rating used the results of functional respiratory investigation expressed as a percentage relative to the normal value (using an international classification method taking into account age and size in particular).

The patients were given a follow-up with at least one consultation at 2 months, 8 months, 12 months, 24 months. The course of the treatments followed and the number of units taken were analyzed.

Table I below gives a clear indication of the very positive results obtained after a treatment time of approximately 8 months. A distinct improvement was noted in the pathological condition of the patients, with a drop in the overall clinical score for severity falling from an average value of 9.56 to 2.47, the standard deviation decreasing from 1.15 to 0.53, confirming the efficacy of the treatment in all patient age and sex groups. The mean number of affected target organs fell from 3.69 to 1.73, while the standard deviation in the number of target organs affected was reduced from 0.49 to 0.41.

TABLE I

| Patient reference | Sex | Date of birth | Date of initial consultation | N° of tests + | Initial consultation N° of target organs affected | Initial consultation Total clinical score | 3rd consultation after 8 months' treatment N° of target organs affected | 3rd consultation after 8 months' treatment Total clinical score |
|---|---|---|---|---|---|---|---|---|
| 1 | M | 1964 | 1996 | 3 | 3 | 7 | 2 | 2 |
| 2 | F | 1936 | 2000 | 4 | 3 | 6 | 1 | 2 |
| 3 | F | 1944 | 1993 | 8 | 4 | 10 | 2 | 2 |
| 4 | F | 1974 | 1997 | 8 | 4 | 9 | 1 | 3 |
| 5 | F | 1950 | 1997 | 8 | 4 | 9 | 2 | 3 |
| 6 | M | 1960 | 1997 | 7 | 4 | 8 | 1 | 2 |
| 7 | F | 1944 | 1996 | 4 | 3 | 6 | 2 | 2 |
| 8 | F | 1963 | 1993 | 4 | 5 | 10 | 1 | 2 |
| 9 | M | 1988 | 1993 | 7 | 4 | 8 | 2 | 2 |
| 10 | M | 1991 | 1993 | 3 | 4 | 9 | 1 | 2 |
| 11 | M | 1971 | 2000 | 6 | 3 | 9 | 1 | 2 |
| 12 | M | 1948 | 2000 | 3 | 4 | 9 | 1 | 2 |
| 13 | M | 1929 | 2000 | 3 | 3 | 7 | 2 | 2 |
| 14 | M | 1953 | 1999 | 5 | 4 | 9 | 1 | 1 |
| 15 | F | 1932 | 1994 | 10 | 4 | 10 | 1 | 2 |
| 16 | F | 1934 | 1996 | 8 | 6 | 11 | 2 | 2 |
| 17 | F | 1982 | 1993 | 5 | 4 | 10 | 2 | 2 |
| 18 | F | 1963 | 1994 | 4 | 4 | 10 | 2 | 2 |
| 19 | M | 1996 | 1996 | 4 | 4 | 10 | 1 | 3 |
| 20 | F | 1991 | 1997 | 5 | 4 | 10 | 2 | 3 |
| 21 | F | 1990 | 1996 | 7 | 3 | 8 | 1 | 2 |
| 22 | F | 1949 | 2000 | 4 | 4 | 8 | 2 | 3 |
| 23 | M | 1995 | 2000 | 3 | 2 | 6 | 1 | 2 |
| 24 | F | 1961 | 1994 | 8 | 3 | 8 | 1 | 2 |
| 25 | M | 1987 | 1994 | 7 | 4 | 9 | 2 | 3 |
| 26 | F | 1991 | 1995 | 8 | 3 | 8 | 1 | 2 |
| 27 | M | 1967 | 1994 | 7 | 3 | 9 | 2 | 2 |
| 28 | M | 1989 | 1994 | 7 | 4 | 9 | 2 | 3 |
| 29 | M | 1947 | 1999 | 5 | 4 | 9 | 2 | 2 |
| 30 | F | 1920 | 1999 | 2 | 3 | 8 | 1 | 2 |
| 31 | F | 1963 | 1997 | 6 | 4 | 9 | 2 | 2 |
| 32 | M | 1979 | 1998 | 4 | 4 | 9 | 1 | 2 |
| 33 | F | 1983 | 2000 | 3 | 3 | 8 | 2 | 2 |
| 34 | M | 1996 | 1999 | 7 | 4 | 8 | 2 | 2 |
| 35 | F | 1946 | 1995 | 7 | 3 | 8 | 2 | 3 |
| 36 | F | 1958 | 1995 | 5 | 4 | 10 | 2 | 2 |
| 37 | F | 1946 | 1997 | 6 | 4 | 11 | 2 | 2 |
| 38 | F | 1965 | 1993 | 3 | 3 | 9 | 1 | 2 |
| 39 | M | 1973 | 2000 | 7 | 4 | 9 | 2 | 2 |
| 40 | M | 1957 | 1995 | 5 | 4 | 9 | 2 | 2 |
| 41 | F | 1942 | 1995 | 8 | 4 | 9 | 2 | 2 |
| 42 | F | 1933 | 1999 | 4 | 3 | 9 | 1 | 3 |
| 43 | F | 1959 | 1999 | 4 | 3 | 8 | 2 | 3 |
| 44 | F | 1965 | 1999 | 3 | 4 | 10 | 2 | 2 |
| 45 | F | 1944 | 1999 | 3 | 4 | 10 | 2 | 3 |
| 46 | F | 1942 | 1996 | 6 | 4 | 11 | 1 | 3 |
| 47 | F | 1948 | 1997 | 6 | 4 | 11 | 2 | 3 |
| 48 | F | 1963 | 1999 | 4 | 4 | 10 | 2 | 2 |
| 49 | M | 1981 | 1999 | 5 | 4 | 12 | 2 | 2 |
| 50 | M | 1995 | 2000 | 5 | 4 | 12 | 2 | 2 |
| 51 | M | 1989 | 1999 | 5 | 4 | 10 | 2 | 2 |
| 52 | M | 1997 | 1998 | 4 | 4 | 10 | 2 | 3 |
| 53 | F | 1997 | 1998 | 5 | 4 | 9 | 1 | 3 |
| 54 | F | 1995 | 1997 | 4 | 4 | 10 | 2 | 3 |
| 55 | F | 1984 | 1993 | 3 | 3 | 9 | 1 | 2 |
| 56 | M | 1969 | 1996 | 10 | 4 | 12 | 2 | 3 |
| 57 | M | 1951 | 1996 | 11 | 4 | 11 | 2 | 2 |
| 58 | M | 1992 | 1997 | 5 | 4 | 11 | 2 | 3 |
| 59 | M | 1975 | 1994 | 4 | 3 | 9 | 1 | 2 |
| 60 | M | 1977 | 2000 | 5 | 4 | 12 | 2 | 3 |
| 61 | M | 1989 | 1993 | 5 | 4 | 12 | 2 | 3 |
| 62 | M | 1994 | 1998 | 8 | 4 | 11 | 2 | 3 |
| 63 | F | 1993 | 1998 | 7 | 4 | 10 | 2 | 2 |
| 64 | F | 1988 | 1993 | 3 | 3 | 9 | 2 | 3 |
| 65 | F | 1940 | 1999 | 4 | 4 | 11 | 2 | 2 |
| 72 | F | 1951 | 2000 | 6 | 4 | 11 | 2 | 3 |
| 73 | F | 1956 | 1999 | 5 | 4 | 11 | 2 | 3 |
| 74 | M | 1982 | 1994 | 4 | 3 | 9 | 2 | 3 |

TABLE I-continued

| Patient reference | Sex | Date of birth | Date of initial consultation | N° of tests + | Initial consulatation ||| 3rd consultation after 8 months' treatment ||
|---|---|---|---|---|---|---|---|---|---|
| | | | | | N° of target organs affected | Total clinical score | | N° of target organs affected | Total clinical score |
| 75 | F | 1944 | 1998 | 3 | 4 | 12 | | 2 | 2 |
| 76 | F | 1992 | 1997 | 7 | 3 | 9 | | 2 | 3 |
| 77 | M | 1997 | 1993 | 4 | 3 | 9 | | 1 | 3 |
| 78 | F | 1955 | 1997 | 5 | 4 | 10 | | 2 | 3 |
| 79 | F | 1996 | 1999 | 4 | 3 | 8 | | 2 | 3 |
| 80 | F | 1936 | 1993 | 5 | 4 | 10 | | 1 | 2 |
| 81 | M | 1949 | 1998 | 5 | 3 | 10 | | 2 | 2 |
| 82 | M | 1966 | 1993 | 4 | 3 | 9 | | 2 | 2 |
| 83 | F | 1963 | 2000 | 5 | 4 | 10 | | 1 | 2 |
| 84 | F | 1954 | 1993 | 5 | 4 | 11 | | 2 | 2 |
| 85 | F | 1995 | 2000 | 4 | 3 | 9 | | 2 | 3 |
| 86 | M | 1988 | 1994 | 6 | 3 | 8 | | 2 | 2 |
| 87 | F | 1969 | 1997 | 6 | 4 | 9 | | 2 | 3 |
| 88 | M | 1963 | 1993 | 5 | 4 | 9 | | 2 | 2 |
| 89 | M | 1994 | 1998 | 7 | 4 | 10 | | 1 | 3 |
| 90 | F | 1992 | 1997 | 6 | 3 | 9 | | 3 | 3 |
| 91 | M | 1988 | 1999 | 6 | 4 | 11 | | 2 | 3 |
| 92 | M | 1955 | 1993 | 6 | 4 | 11 | | 2 | 3 |
| 93 | M | 1944 | 1996 | 7 | 4 | 13 | | 2 | 3 |
| 94 | M | 1986 | 1994 | 6 | 4 | 12 | | 2 | 3 |
| 95 | M | 1954 | 1996 | 6 | 4 | 11 | | 2 | 3 |
| 96 | F | 1989 | 1993 | 6 | 4 | 12 | | 2 | 2 |
| 97 | M | 1965 | 1995 | 6 | 3 | 8 | | 2 | 3 |
| 98 | M | 1986 | 1994 | 4 | 3 | 9 | | 2 | 4 |
| 99 | F | 1956 | 1995 | 4 | 4 | 10 | | 2 | 3 |
| 100 | F | 1944 | 1993 | 2 | 3 | 9 | | 1 | 3 |
| 101 | F | 1995 | 1998 | 5 | 3 | 9 | | 2 | 4 |
| 102 | M | 1960 | 1996 | 3 | 3 | 8 | | 2 | 3 |
| 103 | F | 1928 | 1995 | 6 | 4 | 10 | | 2 | 3 |

Table II below gives the mean clinical score and the standard deviation in the scores obtained.

TABLE II

| | INITIAL VISIT | VISIT AT 8 MONTHS |
|---|---|---|
| MEAN CLINICAL SCORE | 9.56 | 2.47 |
| STANDARD DEVIATION IN SCORES | 1.15 | 0.53 |

Table III below illustrates the average number of target organs affected and the standard deviation in the number of target organs affected.

TABLE III

| | INITIAL VISIT | VISIT AT 8 MONTHS |
|---|---|---|
| MEAN N° OF AFFECTED TARGET ORGANS (T. O.) | 3.69 | 1.73 |
| STANDARD DEVIATION IN N° AFFECTED T.Os. | 0.49 | 0.41 |

The invention claimed is:

1. An anti-allergic pharmaceutical composition comprising
   (a) an acarid allergen consisting of
      i. the allergen as shown in SEQ ID NO:3,
      ii. the allergen as shown in SEQ ID NO:4, and/or
      iii the allergen as shown in SEQ ID NO:5,
   (b) an antihistamine selected from the group consisting of brompheniramine, cetirizine, fexofenadine, cyproheptadine, dexchlorpheniramine, hydroxizine, ketotifene, loratidine, mequitazine, oxotomide, mizolastine, ebastine, astemizole, carbinoxamide, alimemazine, buclizine, cyclizine hydrochlorate and doxylamine,
   (c) an inhibitor of histamine synthesis, wherein the inhibitor comprises an inhibitor of histidine decarboxylase, and
   (d) a pharmaceutically acceptable carrier.

2. The pharmaceutical composition of claim 1, wherein the acarid allergen is *D. Pteronyssinus*.

3. The pharmaceutical composition of claim 1, wherein the acarid allergen is *D. Farinae*.

4. The pharmaceutical composition of claim 1, wherein the acarid allergen is a cystine protease.

5. A method for treating an allergic hypersensitivity reaction comprising administration of the pharmaceutical composition of claim 1 to a subject.

6. The method of claim 5, wherein the allergic hypersensitivity reaction is reduced in the subject.

7. The pharmaceutical composition of claim 1, wherein the acarid allergen is present in an amount of 1 to 1500 micrograms or 10 to 150 micrograms.

8. The pharmaceutical composition of claim 1, wherein the antihistamine is present in an amount of 1 to 2000 milligrams or 5 to 200 milligrams.

9. The pharmaceutical composition of claim 1, wherein the inhibitor of histamine synthesis is present in an amount of between 1 to 2000 milligrams, 5 to 200 milligrams or 10 to 300 milligrams.

10. The pharmaceutical composition of claim 8, wherein the inhibitor of histidine decarboxylase is tritoqualine.

* * * * *

```
                        SEQUENCE LISTING

<160> NUMBER OF SEQ ID NOS: 7

<210> SEQ ID NO 1
<211> LENGTH: 666
<212> TYPE: DNA
<213> ORGANISM: Dermatophagoides pteronyssinus

<400> SEQUENCE: 1
actaacgcct gcagtatcaa tggaaatgct ccagctgaaa tcgatttgcg acaaatgcga      60
actgtcactc ccattcgtat gcaaggaggc tgtggttcat gttggctttt ctctggtgtt     120
```

-continued

```
gccgcaactg aatcagctta tttggctcac cgtaatcaat cattggatct tgctgaacaa    180
gaattagtcg attgtgcttc ccaacacggt tgtcatggtg ataccattcc acgtggtatt    240
gaatacatcc aacataatgg tgtcgtccaa gaaagctact atcgatacgt tgcacgagaa    300
caatcatgcc gaccaccaaa tgcaacaacgt ttcggtatct caaactattg ccaaatttac    360
ccaccaaatg caaacaaaat tcgtgaagct ttggctcaaa cccacagcgc tattgccgtc    420
attattggca tcaaagattt agacgcattc cgtcattatg atggccgaac aatcattcaa    480
cgcgataatg gttaccaacc aaactatcac gctgtcaaca ttgttggtta cagtaacgca    540
caaggtgtcg attattggat cgtacgaaac agttgggata ccaattgggg tgataatggt    600
tacggttatt ttgctgccaa catcgatttg atgatgattg aagaatatcc atatgttgtc    660
attctc                                                                666
```

<210> SEQ ID NO 2
<211> LENGTH: 222
<212> TYPE: PRT
<213> ORGANISM: Dermatophagoides pteronyssinus
<220> FEATURE:
<221> NAME/KEY: PEPTIDE
<222> LOCATION: (1)..(222)
<223> OTHER INFORMATION: Peptide sequence from cystine protease.

<400> SEQUENCE: 2

```
Thr Asn Ala Cys Ser Ile Asn Gly Asn Ala Pro Ala Glu Ile Asp Leu
1               5                   10                  15

Arg Gln Met Arg Thr Val Thr Pro Ile Arg Met Gln Gly Gly Cys Gly
            20                  25                  30

Ser Cys Trp Ala Phe Ser Gly Val Ala Ala Thr Glu Ser Ala Tyr Leu
        35                  40                  45

Ala His Arg Asn Gln Ser Leu Asp Leu Ala Glu Gln Glu Leu Val Asp
    50                  55                  60

Cys Ala Ser Gln His Gly Cys His Gly Asp Thr Ile Pro Arg Gly Ile
65                  70                  75                  80

Glu Tyr Ile Gln His Asn Gly Val Val Gln Glu Ser Tyr Tyr Arg Tyr
                85                  90                  95

Val Ala Arg Glu Gln Ser Cys Arg Arg Pro Asn Ala Gln Arg Phe Gly
            100                 105                 110

Ile Ser Asn Tyr Cys Gln Ile Tyr Pro Pro Asn Ala Asn Lys Ile Arg
        115                 120                 125

Glu Ala Leu Ala Gln Thr His Ser Ala Ile Ala Val Ile Ile Gly Ile
    130                 135                 140

Lys Asp Leu Asp Ala Phe Arg His Tyr Asp Gly Arg Thr Ile Ile Gln
145                 150                 155                 160

Arg Asp Asn Gly Tyr Gln Pro Asn Tyr His Ala Val Asn Ile Val Gly
                165                 170                 175

Tyr Ser Asn Ala Gln Gly Val Asp Tyr Trp Ile Val Arg Asn Ser Trp
            180                 185                 190

Asp Thr Asn Trp Gly Asp Asn Gly Tyr Gly Tyr Phe Ala Ala Asn Ile
        195                 200                 205

Asp Leu Met Met Ile Glu Glu Tyr Pro Tyr Val Val Ile Leu
    210                 215                 220
```

<210> SEQ ID NO 3
<211> LENGTH: 10
<212> TYPE: PRT

```
<213> ORGANISM: Dermatophagoides pteronyssinus
<220> FEATURE:
<221> NAME/KEY: PEPTIDE
<222> LOCATION: (1)..(10)
<223> OTHER INFORMATION: Comprises epitope from cystine protease.

<400> SEQUENCE: 3

Arg Met Gln Gly Gly Cys Gly Ser Cys Asn
1               5                   10

<210> SEQ ID NO 4
<211> LENGTH: 10
<212> TYPE: PRT
<213> ORGANISM: Dermatophagoides pteronyssinus
<220> FEATURE:
<221> NAME/KEY: peptide
<222> LOCATION: (1)..(10)
<223> OTHER INFORMATION: Comprises epitope from cystine protease.

<400> SEQUENCE: 4

Gln Pro Asn Tyr His Ala Val Asn Ile Val
1               5                   10

<210> SEQ ID NO 5
<211> LENGTH: 9
<212> TYPE: PRT
<213> ORGANISM: Dermatophagoides pteronyssinus
<220> FEATURE:
<221> NAME/KEY: peptide
<222> LOCATION: (1)..(9)
<223> OTHER INFORMATION: Comprises epitope from cystine protease.

<400> SEQUENCE: 5

Trp Thr Val Arg Asn Ser Trp Asp Thr
1               5

<210> SEQ ID NO 6
<211> LENGTH: 9
<212> TYPE: DNA
<213> ORGANISM: Dermatophagoides pteronyssinus
<220> FEATURE:
<221> NAME/KEY: primer
<222> LOCATION: (1)..(9)
<223> OTHER INFORMATION:

<400> SEQUENCE: 6 gcggcggcg                                                           9

<210> SEQ ID NO 7
<211> LENGTH: 12
<212> TYPE: DNA
<213> ORGANISM: Dermatophagoides pteronyssinus
<220> FEATURE:
<221> NAME/KEY: primer
<222> LOCATION: (1)..(12)
<223> OTHER INFORMATION:

<400> SEQUENCE: 7
tgagcggcgg cg                                                      12
```